(12) United States Patent
Cheng et al.

(10) Patent No.: US 6,919,491 B1
(45) Date of Patent: Jul. 19, 2005

(54) PROCESS FOR PREPARING SHORT CHAIN ALKYL AROMATIC COMPOUNDS

(75) Inventors: Jane Chi-Ya Cheng, Voorhees, NJ (US); Terry Eugene Helton, Glen Mills, PA (US); Dominick Nicholas Mazzone, Wenonah, NJ (US); Dennis E. Walsh, Richboro, PA (US)

(73) Assignee: ExxonMobil Oil Corporation, Irving, TX (US)

( * ) Notice: Subject to any disclaimer, the term of this patent is extended or adjusted under 35 U.S.C. 154(b) by 844 days.

(21) Appl. No.: 08/853,007

(22) Filed: May 8, 1997

(51) Int. Cl.⁷ .............................................. C07C 4/18
(52) U.S. Cl. ..................................................... 585/475
(58) Field of Search ............................... 585/446, 453, 585/467

(56) References Cited

U.S. PATENT DOCUMENTS

| | | | |
|---|---|---|---|
| 4,429,176 A | 1/1984 | Chester et al. ............... 585/481 |
| 4,522,929 A | 6/1985 | Chester et al. ............... 502/77 |
| 4,582,815 A | 4/1986 | Bowes ........................ 502/64 |
| 4,594,146 A | 6/1986 | Chester et al. ............... 208/111 |
| 4,663,492 A | 5/1987 | Chester et al. ............... 585/408 |
| 4,954,325 A | * 9/1990 | Rubin et al. ................. 423/706 |
| 4,992,606 A | 2/1991 | Kushnerick et al. ......... 585/467 |
| 5,236,575 A | 8/1993 | Bennett et al. ............... 208/46 |
| 5,250,277 A | 10/1993 | Kresge et al. ............ 423/329.1 |
| 5,258,565 A | 11/1993 | Kresge et al. ............... 585/467 |
| 5,292,698 A | 3/1994 | Chu et al. ...................... 502/84 |
| 5,362,697 A | 11/1994 | Fung et al. .................... 502/71 |
| 5,371,310 A | * 12/1994 | Bennett et al. ............. 585/467 |
| 5,453,554 A | 9/1995 | Cheng et al. ............... 585/467 |
| 5,493,065 A | 2/1996 | Cheng et al. ............... 585/467 |

\* cited by examiner

Primary Examiner—Thuan D Dang
(74) Attorney, Agent, or Firm—Darryl M. Tyus; Linda A. Kubena

(57) ABSTRACT

A process for producing alkyl aromatic compounds which comprises contacting at least one aromatic compound with at least one alkylating agent or transalkylating agent possessing at least one aliphatic group having from 1 to 5 carbon atoms under alkylation or transalkylation reaction conditions and in the presence of an alkylation or transalkylation catalyst, to provide an alkylated aromatic product possessing at least one alkyl group derived from said alkylating agent or transalkylating agent, said catalyst comprising a binder-free molecular sieve having an X-ray diffraction pattern that includes the lines set forth in Table A.

4 Claims, 3 Drawing Sheets

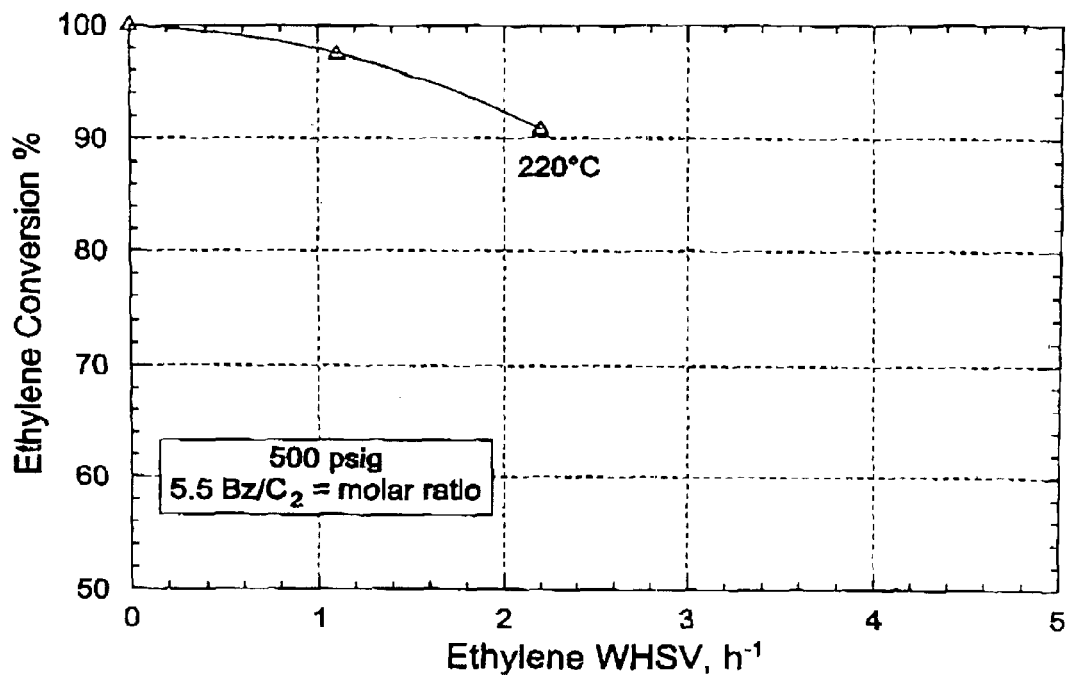
Fig. 1 Ethylbenzene Synthesis with Alumina-Bound MCM-22
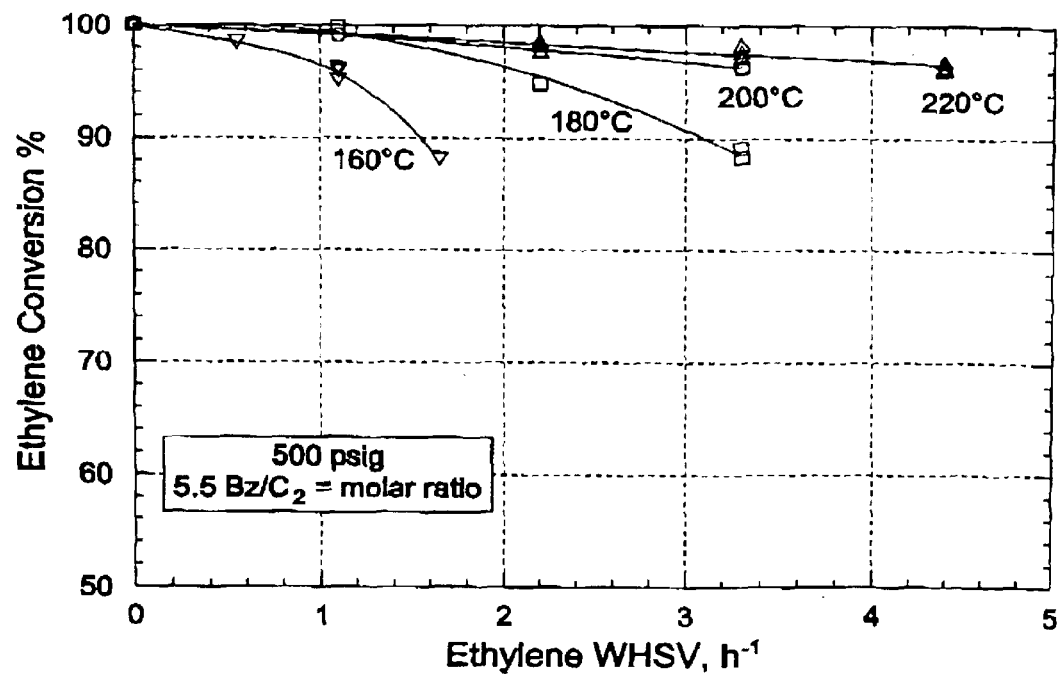
Fig. 2 Ethylbenzene Synthesis with Self-Bound MCM-22

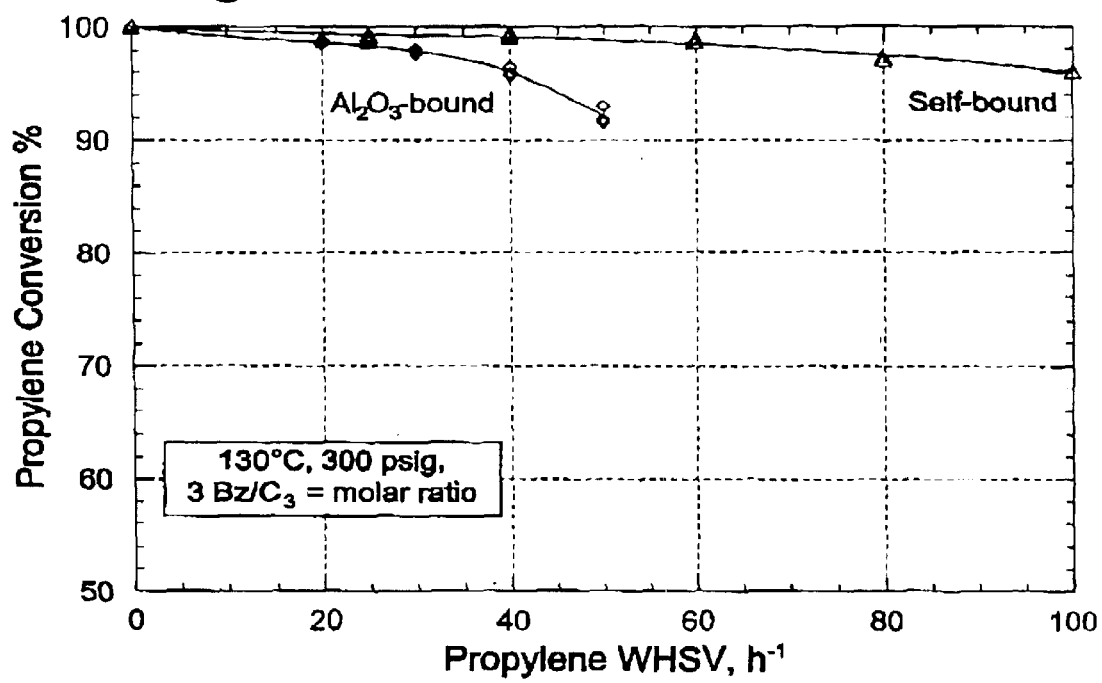
Fig. 3 Cumene Synthesis with MCM-22
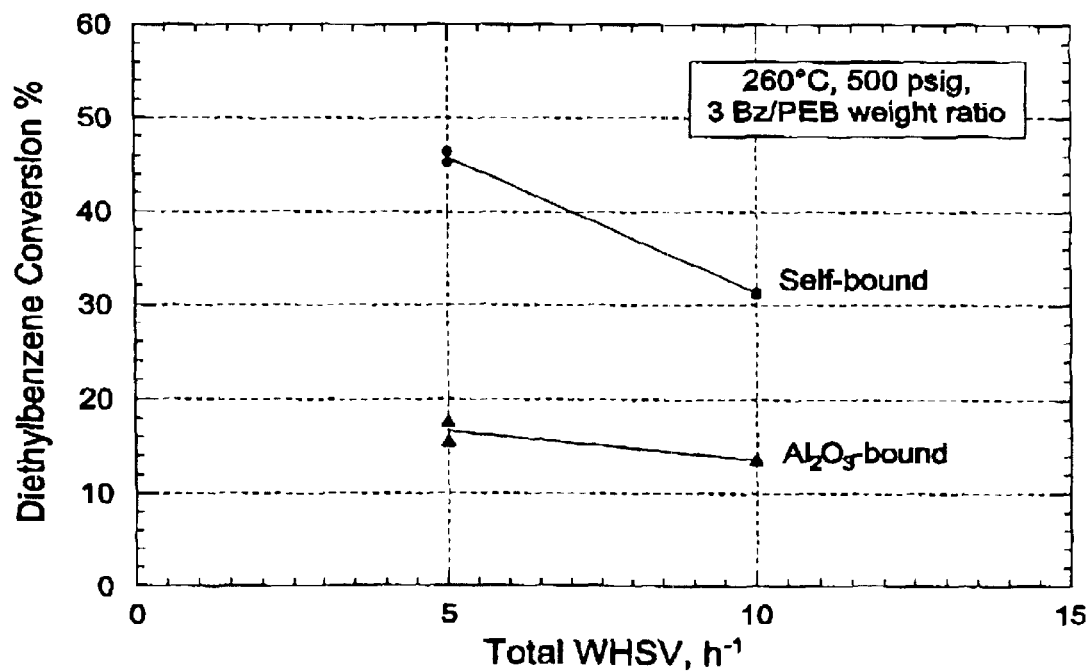
Fig. 4 Ethylbenzene Synthesis via Benzene/PEB Transalkylation with MCM-22

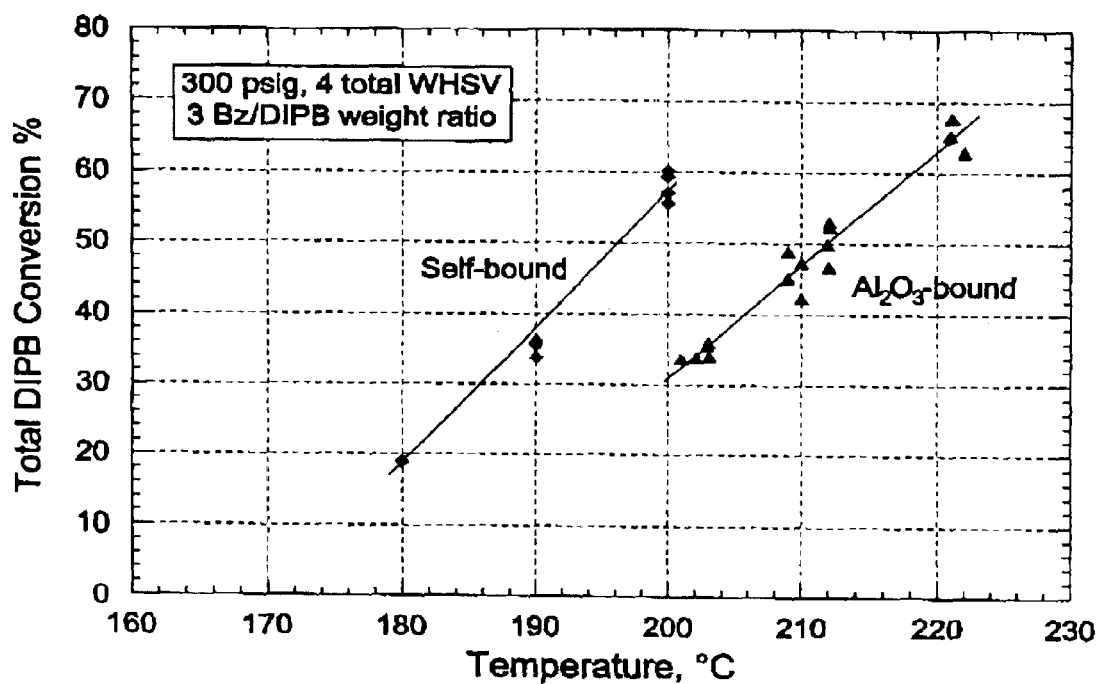
Fig. 5  Cumene Synthesis via Benzene/DIPB Transalkylation with MCM-22

US 6,919,491 B1

PROCESS FOR PREPARING SHORT CHAIN ALKYL AROMATIC COMPOUNDS

BACKGROUND OF THE INVENTION

This invention relates to a process for preparing short chain alkyl aromatic compounds by alkylating an aromatic compound with a relatively short chain alkylating agent, employing a binder-free molecular sieve, as the alkylation catalyst.

Alkylation is one of the most important and useful reactions of hydrocarbons. Lewis and Bronsted acids, including a variety of natural and synthetic zeolites, have been used as catalysts. Alkylation of aromatic hydrocarbon compounds employing certain crystalline zeolite catalysts is known in the art. For example, U.S. Pat. No. 4,992,606, which is incorporated herein by reference, describes the use of an alumina-bound zeolite catalyst, namely an alumina-bound MCM-22 catalyst, in preparing short chain alkyl aromatic compounds, such as cumene.

SUMMARY OF THE INVENTION

It is an object of this invention to provide an improved process for the alkylation of an aromatic compound with a relatively short chain alkylating agent to produce a short chain alkyl aromatic compound, employing an alkylation catalyst comprising a binder-free molecular sieve.

It is a particular object of the present invention to provide a process for alkylating benzene with propylene to produce cumene, or with ethylene to produce ethylbenzene, with limited production of xylenes as a by-product.

It is another particular object of the present invention to provide a process for the alkylation of reformate with fuel gas or other sources of light olefins to produce an alkylate reformate product containing, inter alia, short chain mono- and dialkylates.

A further object of the present invention is to provide an improved process for the transalkylation of an aromatic compound and a transalkylating agent to produce a short chain alkyl aromatic compound, using a transalkylating catalyst comprising a binder-free molecular sieve.

A particular object of the present invention is to provide a process for transalkylating benzene and polyisopropylbenzene or polyethylbenzene to produce cumene or ethylbenzene.

By way of realizing the foregoing and other objects of the invention, a process for preparing short chain alkyl aromatic compounds is provided which comprises contacting at least one aromatic compound with at least one alkylating agent possessing an aliphatic group having from 1 to 5 carbon atoms under alkylation reaction conditions and in the presence of an alkylation catalyst to provide an alkylated aromatic compound possessing at least one alkyl group derived from said alkylating agent, said alkylation catalyst comprising a binder-free molecular sieve.

Further provided is a process for preparing short chain alkyl aromatic compounds comprising contacting at least one aromatic compound with at least one transalkylating agent having two or more aliphatic groups each having from 1 to 5 carbon atoms under transalkylation reaction conditions and in the presence of a transalkylation catalyst comprising a binder-free molecular sieve.

BRIEF DESCRIPTION OF THE FIGURES

FIGS. 1 and 2 compare catalyst activity for liquid phase ethylbenzene synthesis using alumina bound and self-bound MCM-22.

FIG. 3 compares catalyst activity for liquid phase cumene synthesis.

FIG. 4 compares catalyst activity for liquid phase ethylbenzene synthesis.

FIG. 5 compares catalyst activity for liquid phase cumene synthesis via benzene/diisopropylbenzene transalkylation.

DESCRIPTION OF SPECIFIC EMBODIMENTS

The term "aromatic" as used herein includes alkyl substituted and unsubstituted mono- and polynuclear compounds. Compounds of an aromatic character which possess a hetero atom are also useful provided they do not act as catalyst poisons under the reaction conditions selected.

Substituted aromatic compounds which can be alkylated or transalkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation or transalkylation reaction.

Generally the alkyl groups which can be present as substituents on the aromatic compound contain from about one to 22 carbon atoms and preferably from about one to eight carbon atoms, and most preferably from about one to four carbon atoms.

Suitable alkyl substituted aromatic compounds include toluene, xylenes, isopropylbenzene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene, 1,2,3,4,4-tetraethylbenzene, 1,2,3,5-tetramethylbenzene, 1,2,4-triethylbenzene, 1,2,3-trimethylbenzene, m-butyltoluene, p-butyltoluene, 3,5-diethyltoluene, o-ethyltoluene, p-ethyltoluene, m-propyltoluene, 4-ethyl-m-xylene, dimethylnaphthalenes, ethylnaphthalene, 2,3-dimethylanthracene, 9-ethylanthracene, 2-methylanthracene, 1-methylanthracene, 9,10-dimethylphenanthrene, and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecyclbenzene, hexyltoluene, nonyltoluene, dodecyltoluene and pentadecyltoluene. Very often alkylate is obtained as a high boiling fraction in which the alkyl group attached to the aromatic nucleus varies in size from about $C_6$ to $C_{12}$.

Suitable aromatic hydrocarbons include benzene, toluene, xylene, naphthalene, anthracene, naphthacene, perylene, coronene and phenanthrene.

Reformate containing substantial quantities of benzene, toluene and/or xylene constitutes a particularly useful feed for the alkylation process of this invention.

The alkylating agents which are useful in the process of this invention generally include any organic compound having at least one alkylating group having from 1 to 5 carbon atoms that is capable of reaction with the aromatic compound. Examples of suitable alkylating agents are olefins such as ethylene, propylene, the butenes and the pentenes; alcohols (inclusive of mono-alcohols, dialcohols, trialcohols, etc.) such as methanol, ethanol, the propanols, the butanols and the pentanols; aldehydes such as formaldehyde, acetaldehyde, propionaldehyde, butyraldehyde and n-valeraldehyde; and alkyl halides such as methyl chloride, ethyl chloride, the propyl chlorides, the butyl chlorides and the pentyl chlorides.

Mixtures of light olefins are especially useful as alkylating agents in the alkylation process of this invention. Accordingly, mixtures of ethylene, propylene, butenes and/or pentenes, which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents herein. For example, a typical FCC light olefin stream possesses the following composition:

|  | Wt. % | Mole % |
|---|---|---|
| Ethane | 3.3 | 5.1 |
| Ethylene | 0.7 | 1.2 |
| Propane | 14.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

When transalkylation is desired, the transalkylating agent may be a polyalkyl aromatic hydrocarbon containing two or more alkyl groups that each may have from 1 to 5, and preferably 2 to 4 carbon atoms. For example, suitable polyalkyl aromatic hydrocarbons include di-, tri-, and tetraalkyl aromatic hydrocarbons, such as diethylbenzene, triethylbenzene, diethylmethylbenzene (diethyltoluene), diisopropylbenzene, triisopropylbenzene, diisopropyltoluene, dibutylbenzene, and the like. Preferred polyalkyl aromatic hydrocarbons are the dialkyl benzenes. Particularly preferred polyalkyl aromatic hydrocarbons are diisopropylbenzene and diethylbenzene.

Reaction products which may be obtained from the process of the invention include ethylbenzene from the reaction of benzene with either ethylene or polyethylbenzenes, cumene from the reaction of benzene with propylene or polyisopropylbenzenes, ethyltoluene from the reaction of toluene with ethylene or polyethyltoluenes, cymenes from the reaction of toluene with propylene or polyisopropyltoluenes, and secbutylbenzene from the reaction of benzene and n-butenes or polybutylbenzenes. The production of cumene from the alkylation of benzene with propylene or the transalkylation of benzene with diisopropylbenzene is another example of the production of a particular product.

Preferably a synthetic porous crystalline material that is characterized, in its calcined form, by an X-ray diffraction pattern including the following lines, may be used as the binder-free molecular sieve of the present invention:

TABLE A

| Interplaner d-Spacing (A) | Relative Intensity, I/I$_o$ × 100 |
|---|---|
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |

TABLE A-continued

| Interplaner d-Spacing (A) | Relative Intensity, I/I$_o$ × 100 |
|---|---|
| 4.06 ± 0.07 | M-S |
| 3.91 ± 0.07 | M-VS |
| 3.42 ± 0.06 | VS |

Alternatively, the synthetic porous crystalline material may be characterized by an X-ray diffraction pattern in its calcined form including the following lines:

TABLE B

| Interplaner d-Spacing (A) | Relative Intensity, I/I$_o$ × 100 |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, the calcined form may be characterized by an X-ray diffraction pattern including the following lines:

TABLE C

| Interplaner d-Spacing (A) | Relative Intensity, I/I$_o$ × 100 |
|---|---|
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

Most specifically, the synthetic porous crystalline material may be characterized in its calcined form by an X-ray diffraction pattern including the following lines:

TABLE D

| Interplaner d-Spacing (A) | Relative Intensity, I/I$_o$ × 100 |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |

TABLE D-continued

| Interplaner d-Spacing (A) | Relative Intensity, $I/I_o \times 100$ |
|---|---|
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

An example of such a synthetic porous crystalline material is MCM-22, which has a composition that satisfies the molar relationship:

$$X_2O_3:(n)YO_2,$$

wherein X is a trivalent element, such as aluminum, boron, iron and/or gallium, preferably aluminum; Y is a tetravalent element, such as silicon and/or germanium, preferably silicon; and n is at least about 10, usually from about 10 to 150, more usually from about 10 to 60, and even more usually from about 20 to 40. In the as-synthesized form, i.e., before ion exchange, calcination, etc., MCM-22 has a formula, on an anhydrous basis and in term of moles of oxides per n moles of $YO_2$, as follows:

$$(0.005–0.1)Na_2O:(1–4)R:X_2O_3:nYO_2$$

wherein R is an organic component. The Na and R components are associated with the porous crystalline material as a result of their presence during crystallization, and are easily removed by post-crystallization methods hereinafter more particularly described.

MCM-22 is thermally stable and exhibits a high surface area greater than about 400 $m^2$/gm as measured by the BET (Bruenauer, Emmet and Teller) test and unusually large sorption capacity when compared to other crystal structures having similar X-ray diffraction patterns. As is evident from the above formula, MCM-22 is synthesized nearly free of Na cations and thus possesses acid catalyst activity as synthesized. It can, therefore, be used as the alkylation or transalkylation catalyst without having to first undergo an exchange step. To the extent desired, however, the original sodium cations of the as-synthesized material can be replaced in accordance with techniques well known in the art, at least in part, by ion exchange with other cations. Preferred replacement cations include metal ions, hydrogen ions, hydrogen precursor, e.g., ammonium, ions and mixtures thereof. Particularly preferred cations are those which tailor the activity of the catalyst for preparing short chain alkylaromatics. These include hydrogen, rare earth metals and metals of Groups IIA, IIIA, IVA, IIB, IIB, IIIB, IVB and VIII of the Periodic Table of the Elements. In its calcined form, MCM-22 appears to be made up of a single crystal phase with little or no detectable impurity crystal phases.

MCM-22 can be prepared from a reaction mixture containing sources of alkali or alkaline earth metal cation (M), e.g., sodium or potassium; an oxide of trivalent element X, e.g., aluminum; an oxide of tetravalent element Y, e.g., silicon; an organic (R) directing agent; and water, said reaction mixture having a composition, in terms of mole ratios of oxides, within the following ranges:

| REACTANTS | USEFUL | PREFERRED |
|---|---|---|
| $YO_2/X_2O_3$ | 10–60 | 10–40 |
| $H_2O/YC_2$ | 5–100 | 10–50 |
| $OH^-/YO_2$ | 0.01–1.0 | 0.1–0.5 |
| $M/YO_2$ | 0.01–2.0 | 0.1–1.0 |
| $R/YO_2$ | 0.05–1.0 | 0.1–0.5 |

In a preferred method of synthesizing MCM-22, the $YO_2$ reactant contains a substantial amount of solid $YO_2$, e.g., at least about 30 wt. % solid $YO_2$. Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors crystal formation from the above mixture. If another source of oxide of silicon, e.g., Q-Brand (a sodium silicate comprised of about 28.8 wt. % of $SiO_2$, 8.9 wt. % $Na_2O$ and 62.3 wt. % $H_2O$) is used, crystallization may yield little if any MCM-22 crystalline material and impurity phases of other crystal structures, e.g., ZSM-12, may be produced. Therefore the $YO_2$, e.g., silica, source preferably contains at least about 30 wt. % solid $YO_2$, e.g., silica, and more preferably at least about 40 wt. % solid $YO_2$.

The organic directing agent for use in synthesizing MCM-22 from the above reaction mixture is hexamethyleneimine.

Crystallization of the MCM-22 crystalline material can be carried out at either static or stirred conditions in a suitable reactor vessel such as, e.g., polypropylene jars or teflon-lined or stainless steel autoclaves. The useful range of temperatures for crystallization is from about 80° C. to 225° C. for a time sufficient for crystallization to occur at the temperature used, e.g., from about 25 hours to 60 days. Thereafter, the crystals are separated from the liquid and recovered.

Alternatively, MCM-36, MCM49 or MCM-56 may be used as the synthetic porous crystalline material of the present invention. MCM-36 is described in U.S. Pat. Nos. 5,250,277 and 5,292,698, which are incorporated herein by reference. U.S. Pat. No. 5,258,565, also incorporated herein by reference, describes the synthesis of alkylaromatics, including ethylbenzene, using a catalyst comprising MCM-36. MCM-49 and MCM-56 are described in U.S. Pat. No. 5,236,575 and U.S. Pat. No. 5,362,697, respectively, which are incorporated herein by reference. The use of MCM-49 and MCM-56 in the synthesis of alkylaromatics is described in U.S. Pat. Nos. 5,493,065, 5,371,310 and 5,453,554, which are hereby incorporated by reference.

Additionally, aluminosilicates molecular sieve materials such as SAPO's, which contain oxides of elements other than silicon and aluminum, such as phosphorus, may be used as the binder-free molecular sieve of the present invention.

The synthetic porous crystalline material or molecular sieve herein can also be used in intimate combination with a hydrogenating component such as tungsten, vanadium, molybdenum, rhenium, nickel, cobalt, chromium, manganese, or a noble metal such as platinum, palladium, or platinum/palladium combination where a hydrogenation-dehydrogenation function is to be performed. Such component can be introduced by way of cocrystallization, exchanged into the synthetic porous crystalline material or molecular sieve composition to the extent a Group IIIA element, e.g., aluminum, is in the structure, impregnated therein or physically admixed therewith. Such component can be impregnated in, or on, the composition, for example in the case of platinum, by treating the composition with a solution containing a platinum metal-containing ion. Thus, suitable platinum compounds for this purpose include chloroplatinic acid, platinous chloride and various compounds containing the platinum amine complex. Prior to use, the synthetic porous crystalline material or molecular sieve should be subjected to thermal treatment to remove part or all of any organic constituent present therein.

The synthetic porous crystalline material, especially in its metal, hydrogen and ammonium forms, can be beneficially converted to another form by thermal treatment. This thermal treatment is generally performed by heating one of these forms at a temperature of at least about 370° C. for at least 1 minute and generally for no longer than 20 hours. While subatmospheric pressure can be employed for the thermal treatment, atmospheric pressure is preferred simply for reasons of convenience. The thermal treatment can be performed at a temperature of up to about 925° C.

The stability of the synthetic porous crystalline material of the invention may be increased by steaming. U.S. Pat. Nos. 4,663,492; 4,594,146; 4,522,929; and 4,429,176, the entire disclosures of which are incorporated herein by reference, describe conditions for the steam stabilization of the synthetic porous crystalline material herein. The steam stabilization conditions include contacting the catalyst with, e.g., 5–100% steam at a temperature of at least about 300° C. (e.g., 300°–650° C.) for at least one hour (e.g., 1–200 hours) at a pressure of 101–2500 kPa. In a more particular embodiment, the synthetic porous crystalline material can be made to undergo steaming with 75–100% steam at 315°–500° C. and atmospheric pressure for 2–25 hours. In accordance with the steam stabilization treatment described in the above-mentioned patents, the steaming of the synthetic porous crystalline material can take place under conditions sufficient to initially increase the Alpha Value of the catalyst, the significance of which is discussed in U.S. Pat. No. 4,992,606, and produce a steamed catalyst having a peak Alpha Value. If desired, steaming can be continued to subsequently reduce the Alpha Value from the peak Alpha Value to an Alpha Value which is substantially the same as the Alpha Value of the unsteamed catalyst.

Prior to its use in the alkylation or transalkylation process of this invention, the synthetic porous crystalline material or molecular sieve should be dehydrated, at least partially. This can be done by heating the synthetic porous crystalline material or molecular sieve to a temperature in the range of from about 200° C. to 595° C. in an atmosphere such as air, nitrogen, etc. and at atmospheric, subatmospheric or superatmospheric pressures for between about 30 minutes to 48 hours. Dehydration can also be performed at room temperature merely by placing the synthetic porous crystalline or molecular sieve material in a vacuum, but a longer time is required to obtain a sufficient amount of dehydration. The term "binder-free" as used herein describes the synthetic porous crystalline material or molecular sieve as being substantially free or free of binder materials such as clays or metal oxides, i.e., alumina or silica. The alkylation or transalkylation catalyst according to the present invention may be prepared by mulling crystals of the synthetic porous crystalline material or molecular sieve with water, in the absence of a binder material.

Alkylation of an aromatic compound in accordance with the invention is effected by contact of the reactants at a temperature of between about 0° C. and 500° C., and preferably between about 50° C. and 250° C. The reaction generally takes place at pressures of from about 0.2 to 250 atmospheres and preferably from about 1 to 70 atmospheres. The molar ratio of aromatic compound to alkylating agent can be from about 0.1:1 to 50:1, and preferably can be from about 0.5:1 to 5:1. Reaction is suitably accomplished utilizing a feed weight hourly space velocity (WHSV) of between about 0.1 $hr^{-1}$ and 500 $hr^{-1}$ and preferably from 0.5 $hr^{-1}$ to 100 $hr^{-1}$, based upon to total weight of active catalyst.

The alkylation process of this invention can be carried out as a batch-type, semi-continuous or continuous operation utilizing a fixed, fluidized or moving bed catalyst system.

The conditions for transalkylation include a temperature of between about 0° C. and 500° C., and preferably between about 160° C. and 270° C. The transalkylation pressure ranges from about 0.2 to 250 atmospheres and preferably about 1 to 70 atmospheres. The molar ratio of aromatic compound to transalkylating agent can be from about 0.1:1 to 50:1. Reaction is suitably accomplished using a total feed weight hourly space velocity (WHSV) of between about 0.1 $hr^{-1}$ and 500 $hr^{-1}$ and preferably from about 1 $hr^{-1}$ to 20 $hr^{-1}$, based upon the total weight of the catalyst.

In order to more fully illustrate the alkylation and transalkylation process of this invention and the manner of practicing the same, the following examples are presented.

COMPARATIVE EXAMPLE 1

Preparation of 65 wt. % MCM-22/35 wt. % $Al_2O_3$ Catalyst

The $Al_2O_3$-bound MCM-22 catalyst was prepared by mulling 65 parts of MCM-22 (the synthesis of MCM-22 is described in U.S. Pat. No. 4,954,325 assigned to Mobil Oil Corp, the entire disclosure of which is incorporated herein by reference.) and 35 parts of a pseudoboehmite alumina with water. The mulled powder was formed into 1/16" extrudates using a screw-type extruder. After drying at 250° F., the extrudate was calcined with nitrogen at 900° F. After cooling to ambient temperature, the extrudate was exchanged with ammonium nitrate to remove residual sodium. After drying, the extrudate was calcined at 1000° F. in air. The composition of the MCM-22 after calcination was 65 wt. % MCM-22 and 35 wt. % $Al_2O_3$. Catalyst properties are summarized in Table 1.

EXAMPLE 1

Preparation of Binder-free MCM-22 Catalyst

The binder-free MCM-22 catalyst according to the present invention was prepared by mulling 100 parts of MCM-22 crystals (the synthesis of which is described in U.S. Pat. No. 4,954,325) with water. The mulled powder was formed into 1/16" extrudates using a screw-type extruder. After drying at 250° F., the extrudate was exchanged with ammonium nitrate to remove residual sodium. After drying, the extrudate was calcined in nitrogen at 900° F. followed by a calcination at 1000° F. in air. Catalyst properties are summarized in Table 1.

TABLE 1

Physical Properties of the Catalysts

| | 65 wt. % MCM-22/35 wt. % Al$_2$O$_3$ Comparative Example 1 | Binder-free MCM- Example 1 |
|---|---|---|
| Alpha activity | 192 | 279 |
| Real density, g/cc | 2.63 | 2.37 |
| Particle density, g/cc | 0.71 | 0.75 |
| Surface area, m$^2$/g | 403 | 482 |

COMPARATIVE EXAMPLE 2

Liquid Phase Ethylbenzene Synthesis Via Benzene-ethylene Alkylation Over 65 wt. % MCM-22/35 wt. % Al$_2$O$_3$ Catalyst 1.0 g of Al$_2$O$_3$-bound MCM-22 catalyst, prepared in Comparative Example 1 as $\frac{1}{16}$" extrudates, was chopped to $\frac{1}{16}$" length. The catalyst was diluted with sand to 3 cc and charged to an isothermal, down-flow, fixed-bed, $\frac{3}{8}$" o.d. reactor. The catalyst was dried at 125° C. and 1 atm with 100 cc/min of flowing N$_2$ for 2 hours. N$_2$ was turned off. Benzene (reagent grade) was fed into the reactor at 45 WHSV (based on total catalyst weight) for 1 hr and then at 16.7 WHSV while the reactor temperature and pressure were increased to 200° C. and 500 psig, respectively. After the desired temperature and pressure were reached, ethylene (Matheson CP grade) was introduced from a mass flow controller at 1.1 WHSV (5.5 benzeneethylene molar ratio). After lining out, liquid products were collected in a cold-trap and analyzed off-line with a Varian 3700 GC. Off-gas was analyzed with an on-line Carle refinery gas analyzer. Ethylene conversion was determined by measuring unreacted ethylene relative to feed ethylene. Total material balances were 100±2%. The experiment was conducted at 200° C., 500 psig, 1.1–2.2 ethylene WHSV, and 5.5 benzeneethylene molar ratio. Catalyst performance is shown below.

EXAMPLE 2

Liquid Phase Ethylbenzene Synthesis Via Benzene-ethylene Alkylation Over Binder-free MCM-22 Catalyst 1.0 g of binder-free MCM-22 catalyst, prepared in Example 1 as $\frac{1}{16}$" extrudates, was chopped to $\frac{1}{16}$" length. The catalyst was tested with the same procedure described in Comparative Example 2. During the experiment, the effects of temperature (160–220° C.), ethylene WHSV (0.55 to 4.4 h$^{-1}$) were studied at 500 psig and 5.5 benzene/ethylene molar ratio. Catalyst performance is shown below. Comparison of Catalyst Performance for Liquid Phase Ethylbenzene Synthesis FIGS. 1 and 2 compare catalyst activity for liquid phase ethylbenzene synthesis at 500 psig, 5.5 benzeneethylene molar ratio with temperature adjusted between 160 and 200° C. and ethylene WHSV adjusted between 0.55 and 4.4 h$^{-1}$. To achieve a constant ethylene conversion (e.g., 98%) at 220° C., the binder-free MCM-22 could be operated at 3–4 times higher throughput than the Al$_2$O$_3$-bound MCM-22. At constant throughput, the binder-free MCM-22 provided ≧50° C. temperature advantage over the Al$_2$O$_3$-bound MCM-22 to achieve comparable ethylene conversions.

The catalyst performances for liquid phase ethylbenzene synthesis are further compared in Table 2. To achieve comparable conversion at 1.1 ethylene WHSV, the binder-free catalyst could be operated at 161° C. vs. 220° C. with the Al$_2$O$_3$-bound catalyst. To achieve comparable conversion at 220° C., the binder-free catalyst could be operated at 4.4 ethylene WHSV vs. 1.1 ethylene WH SV with the Al$_2$O$_3$ bound catalyst. Ethylbenzene selectivity for the binder-free catalyst, when operated at high throughput, was somewhat lower than the Al$_2$O$_3$-bound catalyst. However, the di- and triethylbenzene could be converted to ethylbenzene in the transalkylator by reacting with benzene.

TABLE 2

Ethylbenzene Synthesis via Benzene/Ethylene Alkylation

| Catalyst | Al$_2$O$_3$-bound MCM-22 | Binder-free MCM-22 | |
|---|---|---|---|
| Reaction Temperature, ° C. | 220 | 161 | 220 |
| Ethylene WHSV | 1.1 | 1.1 | 4.4 |
| Ethylene Conversion, % | 97.4 | 96.7 | 96.9 |
| Days on Stream | 2.0 | 5.4 | 0.4 |
| Product Distribution, wt. % | | | |
| Ethylbenzene | 93.66 | 93.36 | 90.82 |
| Diethylbenzene | 6.02 | 6.22 | 8.48 |
| Triethylbenzene | 0.19 | 0.24 | 0.55 |
| Σ | 99.87 | 99.82 | 99.85 |
| Lights | 0.03 | 0.01 | 0.00 |
| Xylenes | 0.00 | 0.00 | 0.00 |
| n-C$_3$Bz + Cumene | 0.00 | 0.00 | 0.00 |
| sec-C$_4$-Bz | 0.06 | 0.10 | 0.08 |
| Heavies | 0.04 | 0.07 | 0.08 |
| Σ (By Products) | 0.13 | 0.18 | 0.16 |

500 psig and 5.5 benzenethylene molar ratio.

COMPARATIVE EXAMPLE 3

Liquid Phase Cumene Synthesis Via Benzene-propylene Alkylation Over 65 wt. % MCM-22/35 wt. % Al$_2$O$_3$ Catalyst The Al$_2$O$_3$-bound MCM-22 catalyst, prepared in Comparative Example 1 as $\frac{1}{16}$" extrudates, was crushed and sized to 30–40 mesh. 0.25 g of this catalyst was diluted with sand to 3 cc and charged to an isothermal, down-flow, fixed-bed, $\frac{3}{8}$' o.d. reactor. The catalyst was dried at 125° C. and 1 atm with 100 cc/min of flowing N$_2$ for 2 hours. N$_2$ was turned off. Benzene was fed into the reactor at 60 cc/hr for 1 hr and then reduced to desired WHSV (based on total catalyst weight) while the reactor temperature and pressure were increased to 120° C. and 300 psig, respectively. After reaching 120° C. and 300 psig, propylene (Matheson polymer grade) was introduced from a syringe pump at 3 benzene/propylene molar ratio and the temperature was increased to 130° C. After lining out, liquid products were collected in a cold-trap and analyzed off-line with a Varian 3700 GC. Off-gas was analyzed with an on-line Carle refinery gas analyzer. Propylene conversion was determined by measuring unreacted propylene relative to feed propylene. Total material balances were 100±2%. The experiment was conducted at 130° C. average reactor temperature, 300 psig, 10–60 propylene WHSV, and 3 benzene/propylene molar ratio. Catalyst performance is shown below.

EXAMPLE 3

Liquid Phase Cumene Synthesis Via Benzene-propylene Alkylation Over Cinder-free MCM-22 Catalyst The binder-free MCM-22 catalyst, prepared in Example 2 as $\frac{1}{16}$" extrudates, was crushed and sized to 30–40 mesh. 0.1 g of this catalyst was diluted with sand to 3 cc and charged to an isothermal, down-flow, fixed-bed, 3/8' o.d. reactor. The catalyst was tested with the same procedure described in Comparative Example 3. The experiment was conducted at 130° C. average reactor temperature, 300 psig, 15–100 propylene WHSV, and 3 benzene/propylene molar ratio. Catalyst performance is shown below.

Comparison of Catalyst Performance for Liquid Phase Cumene Synthesis

FIG. 3 compares catalyst activity for liquid phase cumene synthesis at 130° C. average reactor temperature, 300 psig, 3 benzene/propylene molar ratio with propylene WHSV adjusted between 10 and 100 h$^{-1}$. To achieve a constant propylene conversion (e.g., 96%) at 130° C. average reactor temperature, the binder-free MCM-22 could be operated at 100 propylene WHSV when compared to 40 propylene WHSV with the $Al_2O_3$-bound catalyst.

The catalyst performances for liquid phase cumene synthesis are further compared in Table 3. When operated at 130° C. and 40 propylene WHSV, the binder-free MCM-22 offered 3% higher propylene conversion than the $Al_2O_3$-bound MCM-22. To achieve 96% propylene conversion at 130° C., the binder-free MCM-22 can be operated at 100 propylene WHSV vs. 40 propylene WHSV with the $Al_2O_3$-bound catalyst. Although cumene,selectivity was somewhat lower with the binder-free MCM-22, the overall alkylation selectivity was higher due to its lower propylene oligomers make. Propylene oligomers are rejected as by-products which reduce net propylene conversion to cumene. The di- and triisopropylbenzene can be converted to cumene in the transalkylator by reacting with benzene.

TABLE 3

Cumene Synthesis via Benzene/Propylene Alkylation

| Catalyst | $Al_2O_3$-bound MCM-22 catalyst | | Binder-free MCM-22 |
|---|---|---|---|
| Propylene WHSV | 40.0 | 40.0 | 100.0 |
| Propylene Conversion, % | 95.9 | 99.2 | 96.0 |
| Days on Stream | 3.3 | 3.5 | 6.2 |
| Product Distribution, wt. % | | | |
| Cumene | 87.03 | 85.73 | 85.65 |
| Diisopropylbenzene | 10.94 | 12.39 | 12.37 |
| Triisopropylbenzene + | 1.01 | 1.17 | 1.11 |
| Σ | 98.98 | 99.29 | 99.13 |
| Propylene Oligomers | 1.01 | 0.69 | 0.84 |
| n-C$_3$-Bz | 0.02 | 0.02 | 0.02 |
| Σ (By Products) | 1.03 | 0.71 | 0.86 |

130° C. average reactor temperature, 300 psig, & 3 benzene/propylene molar ratio.

COMPARATIVE EXAMPLE 4

Liquid Phase Ethylbenzene Synthesis Via Benzene/Polyethylbenzene Transalkylation Over 65 wt. % MCM-22135% wt. % $Al_2O_3$ Catalyst 0.5 g of $Al_2O_3$-bound MCM-22 catalyst, prepared in Comparative Example 1 as 1/16" extrudates, was chopped to 1/16" length. The catalyst was diluted with sand to 3 cc and charged to an isothermal, down-flow, fixed-bed, 3/8" o.d. reactor. The catalyst was dried at 125° C. and 1 atm with 100 cc/min flowing N$_2$ for 2 hours. N$_2$ was turned off and reactor pressure was set to 500 psig by a grove loader. The feed (74.94 wt. % benzene, 23.04 wt. % diethylbenzenes, 0.14 wt. % butylbenzenes, and 1.60 wt. % triethylbenzenes) was fed into the reactor at 60 cc/hr for 1 hour and then at 5 total WHSV. The reactor temperature was then increased to 260° C. After lining out, liquid products were collected in a cold-trap and analyzed off-line with an HP 5890 GC. The catalyst was then tested at 10 WHSV. Total material balances were 100±2%. Catalyst performance is shown below.

EXAMPLE 4

Liquid Phase Ethylbenzene Synthesis Via Benzene/Polyethylbenzene Transalkylation Over Binder-free MCM-22 Catalyst 0.5 g of binder-free MCM-22 catalyst, prepared in Example 1 as 1/16" extrudates, was chopped to 1/16" length. The catalyst was tested with the same procedure described in Comparative Example 4. Catalyst performance is shown below.

Comparison of Catalyst Performance for Liquid Phase Ethylbenzene Synthesis Via Benzene/Polyethylbenzene Transalkylation FIG. 4 compares catalyst activity for liquid phase ethylbenzene synthesis via benzene/polyethylbenzene transalkylation at 260° C., 500 psig, 3:1 benzene/polyethylbenzene weight ratio with total WHSV adjusted between 5 and 10 hr$^{-1}$. The binder-free MCM-22 was significantly more active than the $Al_2O_3$-bound MCM-22.

The catalyst performances of benzene/polyethylbenzene transalkylation are further compared in Table 4. When operated at 5 total WHSV, the binder-free MCM-22 offered about 3-fold higher diethylbenzene, butylbenzene, and triethylbenzene conversions than the $Al_2O_3$-bound MCM-22. At these higher conversions, the binder-free MCM-22 provided 3% higher ethyl benzene selectivity than the $Al_2O_3$-bound MCM-22.

TABLE 4

Ethylbenzene synthesis via benzene/polyethylbenzene transalkylation

| Catalyst | $Al_2O_3$-bound MCM-22 | Binder-free MCM-22 |
|---|---|---|
| Diethylbenzene Conv. % | 15.6 | 45.3 |
| Butylbenzene Conv. % | 7.9 | 20.4 |
| Triethylbenzene Conv. % | 14.3 | 42.0 |
| Hours on Stream | 47.5 | 29.3 |
| Product Selectivity, % | | |
| Lights | 0.40 | 0.14 |
| Toluene | 0.13 | 0.07 |
| Ethylbenzene | 95.17 | 98.39 |
| Xylenes | 0.00 | 0.00 |
| Styrene | 0.00 | 0.00 |
| C9 Aromatics | 0.30 | 0.15 |
| Others | 4.00 | 1.25 |

260° C., 500 psig, 5 total WHSV, and 3:1 benzene/polyethylbenzene weight ratio (74.94 wt. % benzene, 23.04 wt. % diethylbenzenes, 0.14 wt. % butylbenzenes, and 1.60 wt. % triethylbenzenes).

COMPARATIVE EXAMPLE 5

Liquid Phase Cumene Synthesis Via Benzene/Diisopropylbenzene Transalkylation Over 65 wt. % MCM-22/35% wt. % $Al_2O_3$ Catalyst 0.5 g of $Al_2O_3$-bound MCM-22 catalyst, prepared in Comparative Example 1 as 1/16" extrudates, was chopped to 1/16" length. The catalyst was diluted with sand to 3 cc and charged to an isothermal, down-flow, fixed-bed, 3/8" o.d. reactor. The catalyst was dried at 125° C. and 1 atm with 100 cc/min flowing N$_2$ for 2 hours. N$_2$ was turned off and reactor pressure was set to 300 psig by a grove loader. The feed (75.0 wt. % benzene, 8.3 wt. % m-diisopropylbenzene and 16.7 wt. % p-diisopropylbenzene) was fed into the reactor at 60 cc/hr for 1 hour and then at 4 total WHSV (based on total catalyst weight). The reactor temperature was then increased to 200° C. After lining out, liquid products were collected in a cold-trap and analyzed off-line with an HP 5890 GC. The catalyst was further tested at 210° C. and 220° C. under otherwise identical conditions. Total material balances were 100±2%.

EXAMPLE 5

Liquid Phase Cumene Synthesis Via Benzene/Diisopropylbenzene Transalkylation Over Binder-free MCM-22 Catalyst 1.0 g of binder-free MCM-22 catalyst, prepared in Example 1 as ⅛" extrudates, was chopped to ¹⁄₁₆" length. The catalyst was tested at 180° C., 190° C., and 200° C. with the same procedure described in Comparative Example 5. Catalyst performance is compared with that of $Al_2O_3$-bound MCM-22.

Comparison of Catalyst Performance for Liquid Phase Cumene Synthesis Via Benzene/Diisopropylbenzene Transalkylation FIG. 5 compares catalyst activity for liquid phase cumene synthesis via benzene/diisopropylbenzene transalkylation at 300 psig, 4 total WHSV, and 3:1 benzene/diisopropylbenzene weight ratio.

The catalyst performances for benzene/diisopropylbenzene transalkylation are tabulated in Table 5. At ~36% diisopropylbenzene conversion, binder-free MCM-22 can be operated at 190° C. vs. 203° C. with the $Al_2O_3$-bound MCM-22. At ~200° C., binder-free MCM-22 had 67% higher diisopropylbenzene conversion (59.3% vs. 35.6%) when compared with $Al_2O_3$-bound MCM-22.

TABLE 5

Cumene synthesis vie benzene/diisopropylbenzene transalkylation

| Catalyst | $Al_2O_3$-bound MCM-22 | Binder-free MCM-22 | |
|---|---|---|---|
| Temperature, ° C. | 203 | 190 | 200 |
| Diisopropylbenzene Conv. % | 35.6 | 35.8 | 59.3 |
| Days on Stream | 3.9 | 1.0 | 3.0 |
| Product Selectivity, wt % | | | |
| Lights ($C_7$-) | 0.00 | 0.02 | 0.03 |
| Ethylbenzene | 0.11 | 0.15 | 0.15 |
| Cumene | 98.84 | 98.67 | 98.97 |
| n-$C_3$-Bz | 0.07 | 0.06 | 0.10 |
| Triisopropylbenzene | 0.51 | 0.69 | 0.51 |
| Others | 0.47 | 0.41 | 0.24 |

300 psig, 4 total WHSV (based on total catalyst weight), and 3:1 benzene/diisopropylbenzene weight ratio.

What is claimed is:

1. A process for producing alkyl aromatic compounds which comprises contacting benzene with at least one of polyisopropylbenzene or polyethylbenzene under transalkylation reaction conditions and in the presence of a transalkylation catalyst to provide an alkylated aromatic product possessing at least one alkyl group derived from said polyisopropylbenzene or polyethylbenzene, said transalkylation catalyst comprising a synthetic porous crystalline material of MCM-22 and free of binder materials.

2. The process of claim 1, wherein the transalkylation reaction conditions include a temperature of between about 160° C. and 270° C., a pressure of about 1 to 70 amospheres, a total space velocity, WHSV, of from about 1 to 20 and a molar ratio of benzene to polyisopropylbenzene or polyethylbenzene of from about 0.1:1 to 50:1.

3. A process for producing alkyl aromatic compounds which comprises contacting at least one aromatic compound with at least one transalkylating agent possessing at least one aliphatic group having from 1 to 5 carbon atoms under transalkylation reaction conditions and in the presence of a transalkylation catalyst to provide an alkylated aromatic product possessing at least one alkyl group derived from said transalkylating agent, said transalkylation catalyst free of binder materials and prepared by mulling crystals of a synthetic crystalline material of MCM-22 with water.

4. The process of claim 3, wherein the transalkylation reaction conditions include a temperature of between about 160° C. and 270° C., a pressure of about 1 to 70 atmospheres, a total space velocity, WHSV, of from about 1 to 20 and a molar ratio of aromatic compound to transalkylating agent of from about 0.1:1 to 50:1.

* * * * *